United States Patent [19]
Kozaki et al.

[11] Patent Number: 5,807,736
[45] Date of Patent: Sep. 15, 1998

[54] METHOD FOR BIODEGRADATION OF AROMATIC AND CHLORINATED COMPOUNDS USING MICROORGANISM STRAIN FERM BP-5102

[75] Inventors: Shinya Kozaki, Tokyo; Kinya Kato, Yokohama; Tetsuya Yano, Isehara; Takeshi Imamura, Chigasaki, all of Japan

[73] Assignee: Canon Kabushiki Kaisha, Tokyo, Japan

[21] Appl. No.: 454,515

[22] Filed: May 30, 1995

[30] Foreign Application Priority Data

| May 30, 1994 | [JP] | Japan | 6-116268 |
| May 30, 1994 | [JP] | Japan | 6-116269 |
| Jun. 22, 1994 | [JP] | Japan | 6-139903 |
| May 26, 1995 | [JP] | Japan | 7-127671 |

[51] Int. Cl.$^6$ .............. C02F 3/00; C12N 1/00; C12N 1/20; D06M 16/00
[52] U.S. Cl. .............. 435/262.5; 210/601; 424/93.1; 424/93.4; 424/94.1; 435/252.1; 435/264; 435/821; 435/822; 435/843
[58] Field of Search .................. 210/601; 435/262.5, 435/264, 822, 843, 252.1, 821; 424/93.1, 93.4, 94.1

[56] References Cited

U.S. PATENT DOCUMENTS

| 4,380,504 | 4/1983 | Gutnick et al. | 252/356 |
| 4,511,657 | 4/1985 | Colaruotolo et al. | 435/253 |
| 4,877,736 | 10/1989 | Fliermans | 435/183 |
| 4,925,802 | 5/1990 | Nelson et al. | 435/262 |
| 4,959,315 | 9/1990 | Nelson et al. | 435/167 |
| 5,679,568 | 10/1997 | Imamura et al. | 435/262.5 |

FOREIGN PATENT DOCUMENTS

| 0289350 | 11/1988 | European Pat. Off. | C02F 3/34 |
| 2-92274 | 4/1990 | Japan . | |
| 3-292970 | 12/1991 | Japan . | |
| WO93/12042 | 6/1993 | WIPO | C02F 3/00 |

OTHER PUBLICATIONS

Shields et al., "Mutants of *Pseudomonas cepacia* . . . and Trichloroethylene" Appl. & Envir. Microb., vol. 57, No. 7, pp. 1935–1941 (1991).

Nelson, et al., "Aerobic Metabolism of Trichloroethylene by a Bacterial Isolate", Appl. and Environ. Microb., vol. 52, No. 2, pp. 383–384 (1986).

Wackett, et al., "Degradation of Trichloroethylene by Toluene Dioxygenase in Whole–Cell Studies with *Pseudomonas putida* F1", Appl. and Environ. Microb., vol. 54, No. 7, pp. 1703–1707 (1988).

Vandenbergh, et al; "Metabolism of Volatile Chlorinated Aliphatic Hydrocarbons by *Pseudomonas fluorescens*", Appln. and Environ. Microb., vol. 54, No. 10, pp. 2578–2579 (1988).

Wackett, et al. "Survey of Microbial Oxygenases: Trichloroethylene Degradation by Propane–Oxidizing Bacteria", Appln. and Environ. Microb., vol. 55, No. 10, pp. 2960–2964 (1989).

Harker, et al., "Trichloroethylene Degradation by Two Independent Aromatic–Degrading Pathways in *Alcaligenes eutrophus* JMP134", Appl. and Environ. Microb., vol. 56, No. 4, pp. 1179–1181 (1990).

Folsom, et al., "Phenol and Trichloroethylene Degradation by *Pseudomonas cepacia* G4: Kinetics and Interactions between Substrates", Appl. and Environ. Microb., vol. 56, No. 5, pp. 1279–1285 (1990).

Henry, et al., "Influence of a Endogenous and Exogenous Electron Donors and Trichloroethylene Oxidation Toxicity on Trichloroethylene Oxidation by Methanotrophic Cultures from Groundwater Aquifer", Appl. and Environ. Microb., vol. 57, No. 1, pp. 236–244 (1991).

Embley, et al., "*Lactobacullus vaginalis* sp. nov. from the Human Vagina", Int. J. Syst. Bact. vol. 39, No. 3, pp. 368–370 (1989).

Wittenbury, et al., "Enrichment, Isolation and Some Properties of Methane–utilizing Bacteria", J. Gen. Microb., vol. 61, pp. 205–218 (1970).

Beam, et al., "Microbial Degradation of Cycloparaffinic Hydrocarbons via Co–metabolism and Commensalism", J. Gen. Microb., vol. 82, pp. 163–169 (1974).

Dakin, et al., "Lactobacilli Causing Spoilage of Acetic Acid Preserves", J. Appl. Bact., vol. 34, No. 3, pp. 541–545 (1971).

Gibson, et al., "Oxidative Degradation of Aromatic Hydrocarbons by Microorganisms. I. Enzymatic Formation of Catechol from Benzene", Biochemistry, vol. 1, No. 7, pp. 2653–2662 (1968).

Arciero, et al., "Degradation of Trichloroethylene By The Ammonia–Oxidizing Bacterium Nitrosomonas Europaea", Biochem. and Biophys. Res. Comm., vol. 159, No. 2 pp. 640–643 (1989).

Ewers, et al., "Selection of trichloroethene (TCE) degrading bacteria that resist inactivation by TCE", Arch. Microbiol. vol. 154, No. 4, pp. 410–413 (1990).

Ryuichiro Kurane et al, "Biodegradation of linear and aromatic . . . " Rev. Inst. Mex. Pet, 1993, 25(1), pp. 38–45.

Kuasnikov et al, "Characteristics of the distribution of bacteria . . . " Mikrobiol. Zh. (Kiev), 1981, 43(1), 40–4.

Soli et al, "Bacteria which attack petroleum hydro–carbons . . . " Biotechnol. Bioeng. (1972), 14(3), 319–30.

Nayata S., "Degrad . . . By Marine Bact.", Bull Jpn Soc Sci Fish, 1982, pp. 781–786.

Tadasa K., "Degrad . . . By A Microorg.", Agric. Biol Chem 41(6), 1977, 925–30.

*Primary Examiner*—David M. Naff
*Assistant Examiner*—Deborah K. Ware
*Attorney, Agent, or Firm*—Fitzpatrick, Cella, Harper & Scinto

[57] ABSTRACT

A bacterial strain J1 (FERM BP-5102) which can effectively degrade aromatic compounds and/or chlorinated organic compounds such as trichloroethylene (TCE) is disclosed. Also the degradation occurs at a lower temperature such as 15°. Further, a method for purifying waste water, soil or a gas polluted with the above chemical compounds utilizing the bacterium is disclosed.

17 Claims, 7 Drawing Sheets

METHOD FOR BIODEGRADATION OF AROMATIC AND CHLORINATED COMPOUNDS USING MICROORGANISM STRAIN FERM BP-5102

BACKGROUND OF THE INVENTION

1. Field of the Invention

The present invention relates to a novel bacterial strain, a method for the biodegradation of aromatic compounds and/or chlorinated organic compounds such as trichloroethylene (TCE) and dichloroethylene (DCE) by using it, particularly a biodegradation purification method and an environment remediation method which are useful for purification of sewage, waste water and gases containing aromatic compounds and/or chlorinated organic compounds as well as the remediation of soil polluted with them.

2. Related Background Art

In recent years, various researches on the environment have shown that harmful and hardly degradable compounds of various kinds have been accumulated in environment, and its influence on everyday life and ecological systems has been apprehended. Therefore, it is strongly desired to establish technologies for preventing the escalation of environmental pollution and for recovering the polluted environment. One example of technologies for remedying the environments is so-called bioremediation which utilizes the functions of microorganisms to degrade the harmful substances to make them harmless to the environment. This technique can be applied to remedy the environment polluted with chlorinated organic compounds, for example, the site of a semiconductor manufacturing factory, a metal processing factory or a chemical plant etc. Pollution of soil not only hinders the reutilization of the land but also escalates the pollution because the pollutant contaminates the groundwater. In particular, trichloroethylene (TCE) has been widely used in large quantities in cleaning process and often causing large-scale pollution problems in various places. Furthermore, since TCE is hardly degraded by the natural purification function of the environment, the environmental pollution with TCE is very serious. Moreover, there are many reports about the carcinogenicity of TCE, thus the environmental pollution with TCE has become an extremely serious social problem.

As a means for removing TCE from the polluted soil, the vacuum extraction method has been widely used. This method comprises digging a well in the polluted soil, sucking off volatile TCE using a vacuum pump. This method, however, has problems in cost, operability etc., and when this method is actually employed, the recovered TCE remains intact in the gaseous phase. Accordingly, the treatment of the recovered TCE is a large problem to be solved. The same problem is present in treating air pollution. Air pollution will occur in the aforesaid high-technology factories or the like, and the polluted air in the factory cannot be discharged to the atmosphere or environment without removing TCE from the air.

At present, a representative means for removing gaseous TCE includes liquefaction or adsorption to activated carbon. The activated carbon method has difficulty in regenerating the used activated carbon, while the liquefaction method has a problem of extremely high cost because it requires a large-scale apparatus although the concentration of the pollutant in the atmosphere is low. In addition, these methods cannot degrade TCE but merely remove TCE, thus they are far from the essential solution. As is apparent from the foregoing, for the gaseous pollution, an essential purification means which is excellent in economy and operability is also strongly desired.

There is an approach to purify the polluted environment utilizing microorganisms of degradation ability. In water treatment, particularly, the utilization of microorganisms has a long history. Concerning soil and air pollution, however, such an approach has quite a short history, just recently beginning to attract attention. Presumably many studies are now in progress concerning microbial treatment of TCE, but there are only a limited number of reports on the isolation of microorganisms having TCE degrading power. For example, isolated TCE degrading microorganisms are *Welchia alkenophila sero* 5 (U.S. Pat. No. 4,877,736, ATCC53570), *Welchia alkenophila sero* 33 (U.S. Pat. No. 4,877,736, ATCC53571), *Methylosinus trichosporium* OB3b [Whittenbury, R., J. Gen. Microbiol. Vol. 61, pp. 205–218 (1970)], *Acinetobacter sp.* G4 [Nelson, M. J. K. et al., Appl. Environ. Microbiol. Aug. pp. 383–384 (1986); Folsom, B. R. et al., Appl. Environ. Microbiol. May, pp. 1279–1285 (1990); and U.S. Pat. No. 4,925,802, ATCC53617; this bacterium was first assigned to *Pseudomonas cepacia* but then changed to *Acinetobacter sp.*], *Methylomonas sp.* MM2 [Henry, S. M. et al., Appl. Environ. Microbiol., Jan., pp. 236–244 (1991)], *Alcaligenes denitrificans ssp. xylosoxidsans* JE75 [Ewers, J. et al., Arch. Microbiol., Vol. 154, pp. 410–413 (1990)], *Alcaligenes eutrophus* JMP 134 [Harker, A. R. & Kim, Y., Appl. Environ. Microbiol. Apr. pp. 1179–1181 (1990)], *Pseudomonas putida* F1 [Gibson, D. T. et al., Biochem. Vol. 7, pp. 2653–2662 (1968); Wackett, L. P. & Gibson, D. T., Appl. Environ. Microbiol. July pp.1703–1708 (1988)], *Mycobacterium vaccae* JOB5 [Beam, H. W. & Perry, J. J., J. Gen. Microbiol. Vol. 82, pp. 163–169 (1974); Wackett, L. P. et al., Appl. Environ. Microbiol. Nov. pp. 2960–2964 (1989), ATCC29678], *Nitrosomonas europaea* [Arciero, D. et al., Biochem. Biophys. Res. Comm. Vol. 159 pp. 640–643 (1989)], *Pseudomonas fluorescens* PFL12 [Vandenbergh, P. A. & Kunka, B. S., Appl. Environ. Microbiol. Oct. pp. 2578–2579 (1988)], *Lactobacillus fuctivorans* RE [Kunkee, Int. J. Syst. Bact., Vol. 30, pp. 313–314 (1980), J. Appl. Bact., Vol. 34, pp. 541–545 (1971)], *Lactobacillus vaginalis sp.* nov. [Embley, T. M. et al., Int. J. Syst. Bacteriol. Vol. 39 pp. 368–370 (1989), ATCC49540], and *Methylosinus trichosporium* (Japanese Patent Application Laid-Open Nos. 2-92274 and 3-292970).

None of the presently known bacteria can satisfy the practical requirements and also have high degradation performance when used for microbial TCE degradation.

Hence, it is now strongly desired to obtain novel microbial strains having the practically required features.

Most of these bacteria are methane-degrading bacteria, requiring methane or ethanol for TCE degradation. Hence, the presently known strains are not satisfactory for soil remediation or air treatment. Accordingly, it is required to obtain new bacterial strains. It is expected that a new strain may have growth conditions different from the known strains in addition to the TCE degrading ability, thus it can widen the application range, or increase the application modes. For example, when an organism is used for the treatment of TCE-polluted soil or air containing TCE, it should not only possess TCE-degrading power, but also show the resistance to the polluted environment, propagation under poor circumstances, and maintenance of TCE degrading ability. That is to say, in view of practice, it is expected for the novel bacteria that the new strain is resistant to chemical substances which are harmful to many microorganisms and can maintain the TCE degrading ability at a high level even at a temperature lower than the optimum growth temperature. As is apparent from the foregoing, it is strongly required an environment remediation method utilizing microorganisms having a TCE degrading power and more advantageous practical characteristics in comparison with the conventionally known strains.

SUMMARY OF THE INVENTION

An object of the present invention is to provide a novel microorganism having powerful ability to decompose aromatic compounds and/or chlorinated organic compounds.

Another object of the present invention is to provide a method for degrading aromatic compounds and/or chlorinated organic compounds, particularly aromatic compounds and/or chlorinated organic compounds in sewage or waste water, by utilizing a novel microorganism.

Still another object of the present invention is to provide a method for remedying soil polluted with aromatic compounds and/or chlorinated organic compounds, utilizing a novel microorganism which can degrade aromatic compounds and/or chlorinated organic compounds.

A further object of the present invention is to provide a method to purify a gas polluted with aromatic compounds and/or chlorinated organic compounds utilizing the novel microorganism which can degrade aromatic compounds and/or chlorinated organic compounds.

The above-mentioned objects can be achieved by the following present invention.

The first aspect of the present invention is a novel bacterium strain J1 (Deposition number in National Institute of bioscience and Human Technology, Agency of Industrial Science and Technology, No. FERM BP-5102 ).

The second aspect of the present invention is a biological treating method for a medium polluted with aromatic compounds and/or chlorinated organic compounds, which comprises the degradation step of aromatic compounds and/or chlorinated organic compounds by bringing strain J1 into contact with the medium polluted with aromatic compounds and/or chlorinated organic compounds.

DETAILED DESCRIPTION OF THE PREFERRED EMBODIMENTS

Figure 1:
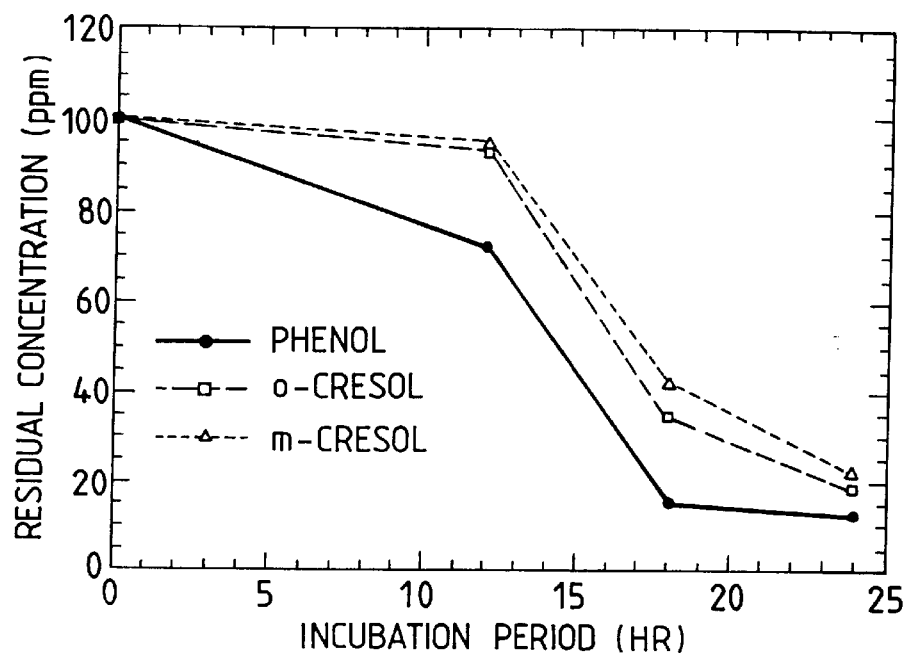
FIG. 1 is a graph showing the degradation of phenolic compounds by strain J1.

The inventors of the present invention widely screened microorganisms capable of degrading aromatic compounds and/or chlorinated organic compounds, and from the soil polluted with aromatic compounds and/or chlorinated organic compounds a novel bacterial strain was obtained which can degrade aromatic compounds and/or chlorinated organic compounds of high concentration. Thus, a method for degrading environmental aromatic compounds and/or chlorinated organic compounds was found applying this microorganism to the environment containing aromatic compounds and/or chlorinated organic compounds.

The bacteriological characteristics of the novel strain of the present invention are as follows:

A. Morphology

Gram stain: Positive

Size and shape of cell: Pleomorphic rod of about 0.5–2 μm by 1–6 μm.

Mobility: Non-motile

Colony: Sticky, creamy to light pink in color

B. Growth in culture media

BHIA: Good growth

MacConkey: No growth

C. Optimum growth temperature: 25° C.>30° C.>35° C.

D. Physiological characteristics

Aerobic/Anaerobic: Aerobic

TSI (slant/stub): Alkali/alkali, $H_2S$(-)

Oxidase: Negative

Catalase: Positive

Fermentation of sugars
  Glucose: Negative
  Sucrose: Negative
  Raffinose: Negative
  Galactose: Negative
  Maltose: Negative Urease: Positive Esculin: Positive Nitric acid: Negative This bacterium is designated as strain J1.

As is apparent from examples given below, this bacterium has an excellent ability to degrade chlorinated organic compounds. Since various known species cannot degrade chlorinated organic compounds under aerobic conditions, this species is thought novel and designated as strain J1. It was deposited in National Institute of Bioscience and Human Technology, Agency of Industrial Science and Technology (Deposition No. FERM BP-5102). at 1–3, Higashi 1-chome, Tsukuba-shi, Ibaraki-ken, 305 Japan, on May 17, 1995.

As described in the examples given below, strain J1 has a feature that it maintains relatively high activity to degrade chlorinated organic compounds even at a low temperature such as about 15° C. In general, the temperature of waste water or the soil temperature to be treated is in the range of 10°–20° C. which is lower than usual optimum growth temperatures of microorganisms. Also to J1 strain, this temperature is lower than its optimum growth temperature, but it can maintain the activity to degrade chlorinated organic compounds sufficient for practical use, dispensing with facilities and cost for heating the waste water or soil. The treatment without heating can prevent the diffusion of highly volatile chlorinated organic compounds into the air. In addition, as described hereinafter, J1 strain can also degrade phenol, cresol etc. and naturally resistant to these organic compounds. These chemicals are harmful to many microorganisms as known from that they are usually used as disinfectants, and often contained in the waste water, the soil or the gas to be treated. J1 strain can degrade chlorinated organic compounds even in the circumstance containing these chemical substances without being killed or losing the degrading activity.

The culture of strain J1 can be carried out in any ordinary culture medium for Corynebacterium, but especially good growth is obtained in 2YT medium. Alternatively, the strain can be cultured in an inorganic salts medium, for example, M9 medium containing a small amount of sodium glutamate as a carbon source, although growth is slow.

2YT medium (in 1 liter)
Polypeptone 16 g
Yeast extract 10 g
NaCl 5 g
(pH 7.2)
M9 medium (in 1 liter)
$Na_2HPO_4$ 6.2 g
$KH_2PO_4$ 3.0 g
NaCl 0.5 g
$NH_4Cl$ 1.0 g
(pH 7.0)

The cultivation can be carried out under aerobic conditions in liquid or on solid. Cultivation temperature is preferably about 30° C.

Spontaneous or artificial mutants of strain J1 are also included in the conception of the present invention, so long as the good activity to degrade aromatic compounds and/or chlorinated organic compounds is maintained.

The treatment for degrading aromatic compounds and/or chlorinated organic compounds in the present invention is carried out by bringing the above-mentioned strain J1 into contact with these compounds in an aqueous medium such as waste water, soil or a gaseous phase. The contact of the microorganism with these compounds in an aqueous medium is accomplished by culturing the microorganism in the aqueous medium containing aromatic compounds and/or chlorinated organic compounds, or by adding the aqueous medium to the culture system of the microorganism, in a batch mode, a semicontinuous mode or a continuous mode. The microorganism can be used in a semi-immobilized or immobilized state on a suitable carrier. If necessary, the waste or the like to be treated may be subjected to various pretreatment, for example, the regulation of the concentrations of aromatic compounds and/or chlorinated organic compounds, adjustment of pH, or replenishment of nutrients. It is preferable to adjust the concentration of aromatic compounds and/or chlorinated organic compounds to about 10 ppm or less in the treatment system.

When aromatic compounds and/or chlorinated organic compounds in soil are to be degraded, the microorganism can be used in the free state or in the immobilized state on a suitable carrier. In addition, if necessary, the subject polluted soil may be treated with other methods such as replenishment of various kinds of nutrients.

To degrade aromatic compounds and/or chlorinated organic compounds in the gas phase, the polluted gas may be introduced into a culture tank in which J1 strain has been cultured, at a predetermined flow rate. Although no particular restriction is put on the technique for the gas introduction, it is preferable to agitate the culture medium by introduction of the gas to accelerate aeration. The introduction and exhaust of the gas may be continuously carried out, intermittently or batch-wise in compliance with a treatment performance. These conditions are preferably optimized by controlling the system in accordance with the concentrations of remaining aromatic compounds and/or chlorinated organic compounds.

According to another culture procedure, cells of J1 strain are attached to a carrier such as soil particles to fill the reactor with them. Next, the gas polluted with aromatic compounds and/or chlorinated organic compounds is introduced into the reactor to degrade them. The carrier to be used is not limited to the soil particles and any one is utilizable so long as it has an excellent microorganisms-retaining property and does not impair air permeability. As the material providing habitat for the microorganism, there can be available various carriers which have been widely employed for bioreactors in waste water treatment systems, pharmaceutical industries and food industries. More concretely, examples of such carriers include particulate carriers such as porous glass, ceramics, metal oxides, activated carbon, kaolinite, bentonite, zeolite, silica gel, alumina and anthracite, gel-like carriers such as starch, agar, chitin, chitosan, polyvinyl alcohol, alginic acid, polyacrylamide, carrageenan, agarose and gelatin, ion exchange celluloses, ion exchange resins, cellulose derivatives, glutaraldehyde, polyacrylic acids, polyurethanes and polyesters. Examples of usable natural carriers include cotton, hemp and paper.

The simplest way to make the microorganism attach on the carrier is to bring the culture of the microorganism and the carrier in contact.

As a growth medium for strain J1, ordinary bacterial growth media can be used. Examples of suitable growth media include bouillon medium, M9 medium, 2YT medium, L medium and a medium containing carbon sources such as glucose, and polypeptone and/or yeast extract. These culture media may be used in a liquid state, or it may be used in gelled state by adding agarose.

In addition, as materials providing both nutrients and habitats for the microorganism, agricultural compost presents good examples. That is to say, examples of such materials include dried plant materials such as cereal straws, sawdust, rice bran, bean curd refuse and bagasse, as well as marine wastes such as crab or shrimp shells.

For the purification of the gas polluted with aromatic compounds and/or chlorinated organic compounds, a container is filled first with a carrier material and then the microbial cells, or the microorganism may be first cultured in the container and then the carrier may be introduced. In order to efficiently perform the degrading reaction, conditions such as the nutrients, water content and oxygen concentration must be suitably maintained. The ratio of the carrier to the water content in a reactor should be suitably selected in consideration of the microbial growth and air penetration, and the shape of the reactor may be suitably selected in consideration of the volume and concentration of the gas to be treated, preferably considering acceleration of the contact of the gas with the microorganisms supported on the carrier. For example, the shape of the reactor may be a column, a tube, a tank or a box. Such a reactor may be unified with an exhaust duct or a filter, or some reactors may be continuously connected to each other in compliance with its performance.

Sometimes the polluted gas is first adsorbed by the carrier material. In that case, however, the adsorbed pollutant may be degraded and the vacant surface of the carrier can newly adsorb the pollutant recovering the adsorbing properties, although the benefit of the microbial treatment cannot be observed in a rare occasion. In this way, the capability to remove aromatic compounds and/or chlorinated organic compounds by the carrier-bound microorganism is not saturated and the constant degradation effect can always be expected.

All the known wild type bacteria capable of degrading a chlorinated organic compound require the presence of a chemical substance called an inducer to exert the degrading activity. That is to say, the enzyme expressed to degrade the inducer can also degrade the target chlorinated organic compound. For example, methane is the inducer for *Methylosinus trichosprium* OB3b, and specific aromatic compounds such as phenol for *Pseudomonas cepacia* KKO1. Strain J1 requires certain aromatic compound as the inducer, and it has been confirmed that at least phenol, o-cresol and m-cresol can function as the inducer. Therefore, in order to degrade chlorinated organic compounds by the use of the microorganism of the present invention, the inducer must be supplied so as to be always present in the degradation system. The effective concentration of the inducer is preferably in the range of 10 to 500 ppm, more preferably 50 to 200 ppm.

The inducer is converted by the present microorganism to a compound of ready-to-degrade, so that it can be completely degraded by passing it through an ordinary waste water treating tank or the like without any problem.

The method of the present invention can be applied to the waste water treatment and the remediation of the polluted soil in both open and closed systems. The microorganism may be immobilized on the carrier and various methods for accelerating the growth may be used together.

The present invention will be described in detail with reference to examples, but the scope of the present invention should not be limited to these examples at all.

EXAMPLE 1

Degradation of Aromatic Compounds by Strain J1

A colony of strain J1 on the agar plate was picked up and inoculated into three test tubes containing 5 ml of M9 medium containing 100 ppm of phenol, o-cresol and m-cresol, respectively. They were incubated with shaking at 30° C. Samples were withdrawn at predetermined intervals, and cells were removed by filtration with a filter of 0.22 $\mu$m pore size. Then the concentrations of phenol, o-cresol and m-cresol in the resultant filtrates were measured by means of a spectrophotometer. The results are shown in FIG. 1.

Each aromatic compound was degraded within 12 to 18 hours, and the culture turned yellow with degradation product(s). The cell number increased due to the assimilation of the aromatic compound, from the initial number of about $10^6$ cells/ml to the final number of about $10^8$ cells/ml.

EXAMPLE 2

Degradation of TCE by Strain J1

In a Sakaguchi flask (a shouldered culture flask), 250 ml of 2YT medium was inoculated with a colony of J1 strain on the agar medium and shake culture was carried out at 30° C. for 24 hours.

Figure 2:
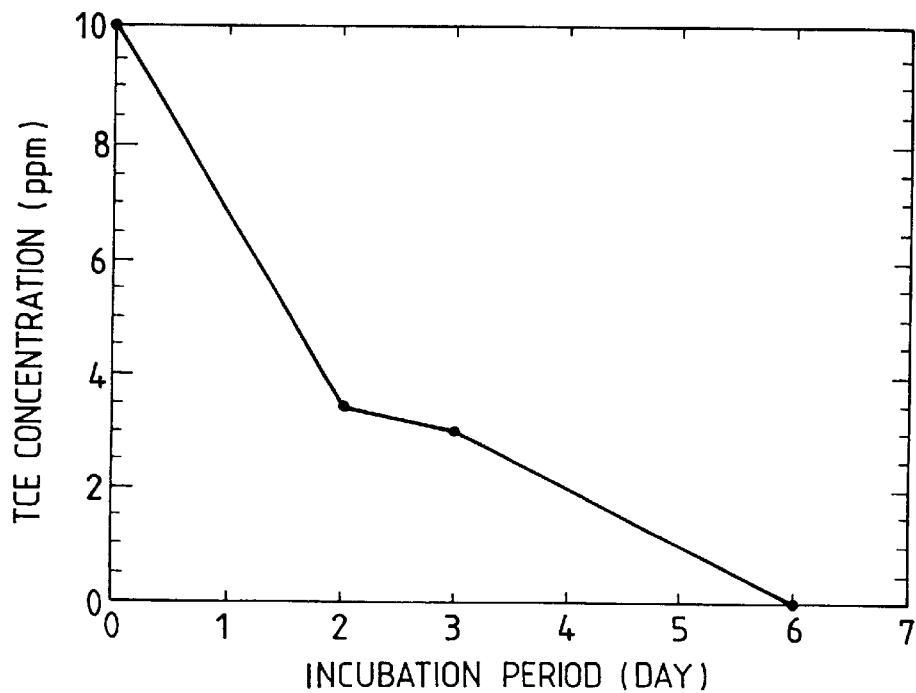
FIG. 2 is a graph showing the degradation of TCE by strain J1 in a phenol-added system.
Figure 3:
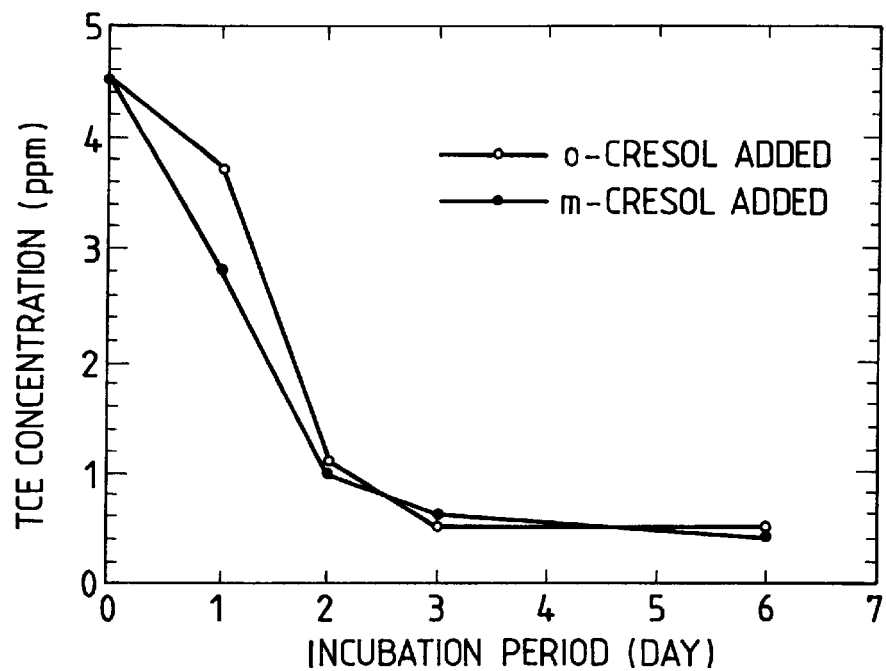
FIG. 3 is a graph showing the degradation of TCE by strain J1 in a cresol-added system.

Next, vials containing 30 ml of M9 medium supplemented with 0.2% sodium glutamate and about 100 ppm of TCE and 100 ppm of phenol, o-cresol or m-cresol as an inducer were prepared and each vial was inoculated with 0.1 ml of the above-mentioned culture of strain J1. Afterward, each vials was completely sealed with a butyl rubber stopper and an aluminum seal, and incubated with shaking at 30° C. The decrease of TCE was determined at predetermined intervals, analyzing the head space gas by gas chromatography. The results are shown in FIGS. 2 and 3.

In the system containing phenol, the amount of TCE decreased to about 35% of the initial concentration within first 2 days, and in the system containing o-cresol or m-cresol, the amount of TCE decreased to about 55%. Considering that the degradation occurred at the TCE concentration as high as about 10 ppm, the degradation speed of J1 strain is on the top level among the known TCE degrading bacteria.

EXAMPLE 3

Figure 4:
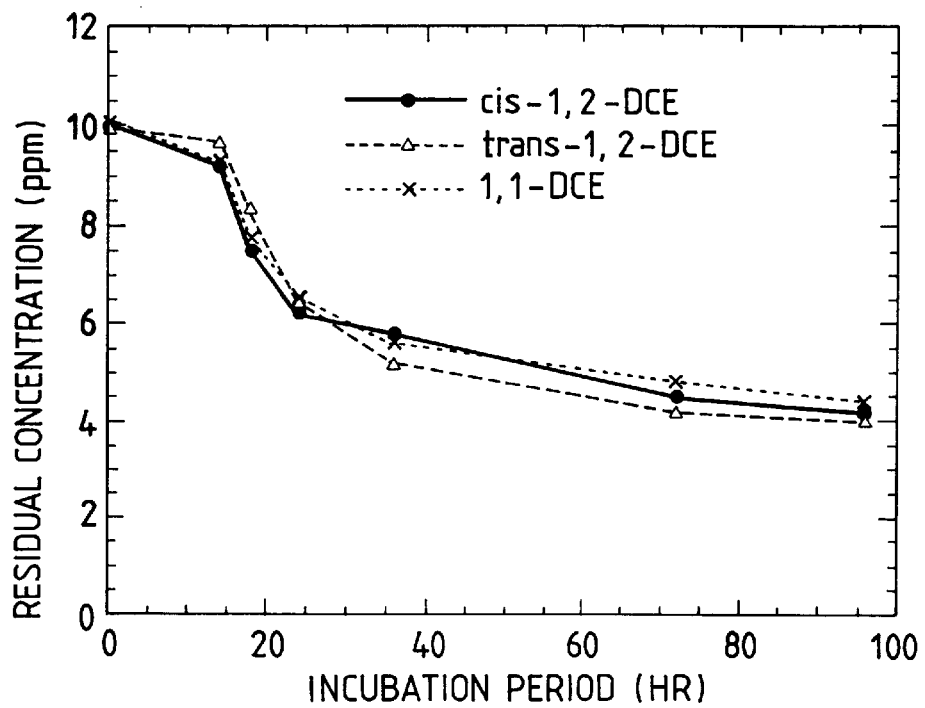
FIG. 4 is a graph showing the degradation of DCE by strain J1.

The decrease of dichloroethylene was measured periodically in the same manner as in Example 2, except that the compound to be degraded was 10 ppm of cis-1,2-dichloroethylene (cis-1,2-DCE) trans-1,2-dichloroethylene (trans-1,2-DCE) or 1,1-dichloroethylene and that the inducer was phenol. The results for cis-1,2-dichloroethylene (cis-1,2-DCE) trans-1,2-dichloroethylene (trans-1,2-DCE) and 1,1-dichloroethylene (1,1-DCE) are shown in FIG. 4.

EXAMPLE 4

Degradation of TCE by Strain J1 at 15° C.

Figure 5:
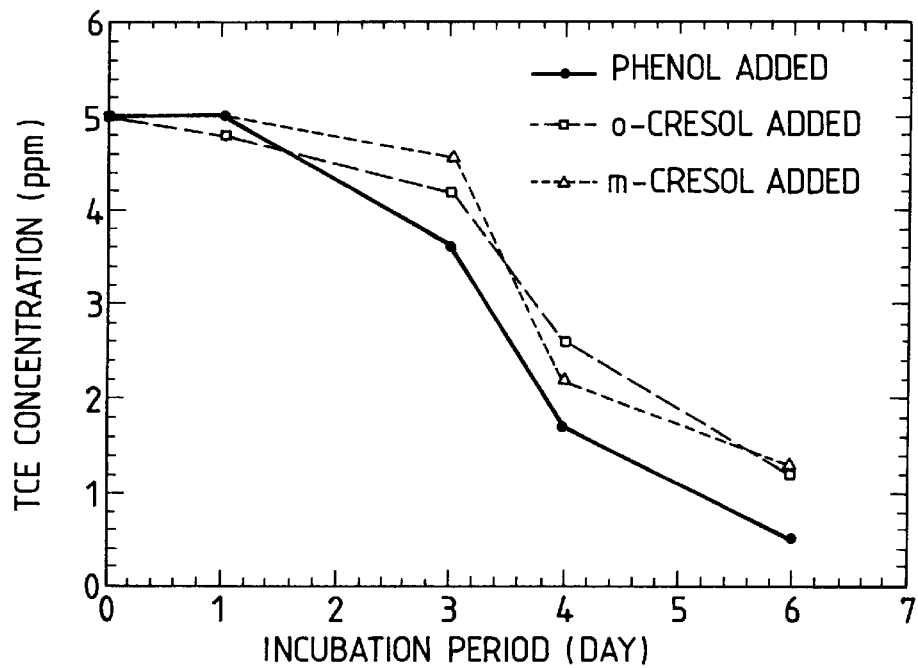
FIG. 5 is a graph showing the degradation of TCE by strain J1 at 15° C.

Following the same procedure as in Example 2, except that 100 ppm of phenol was used and incubation was carried out at 15° C., the amount of TCE was measured at predetermined intervals. The results are shown in FIG. 5.

As compared with cultivation at 30° C., degradation was delayed by about 2 days, but it was apparent that even at a low temperature of 15° C., TCE-degrading activity was maintained at a practical level.

EXAMPLE 5

Degradation of Aromatic Compounds in Soil by Strain J1

A colony of J1 strain on 2YT agar medium was inoculated into 50 ml of 2YT medium in a Sakaguchi flask, and cultured at 30° C. for 24 hours.

Figure 6:
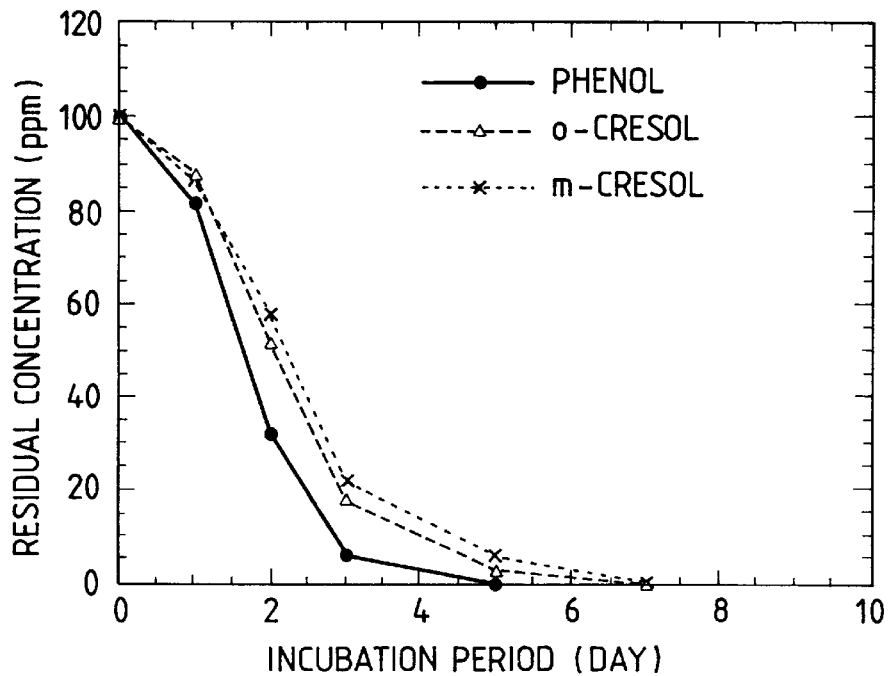
FIG. 6 is a graph showing the degradation of the aromatic compounds in soil.

Next, vials containing 30 ml of M9 medium (0.2% sodium glutamate), supplemented with 100 ppm of phenol, o-cresol and m-cresol respectively were prepared, into each of which sterilized brown forest soil was added up to the liquid surface. Afterward, 0.1 ml of the above-mentioned J1 strain culture was added to each vial and the vial was completely sealed with a butyl rubber stopper and an aluminum seal. Shake culture was then carried out at 30° C. The concentration of phenol was determined by a JIS method using aminoantipyrine (JIS K0102-1993, 28.2). The results are shown in FIG. 6.

EXAMPLE 6

Degradation of TCE in Soil by Strain J1 (30° C.)

A colony of J1 strain on 2YT agar medium was inoculated into 50 ml of 2YT medium in a Sakaguchi flask, and cultured at 30° C. for 24 hours.

Next, vials containing 30 ml of M9 medium (0.2% sodium glutamate), 10 ppm of TCE, and 100 ppm of phenol, o-cresol or m-cresol as an inducer were prepared, into which sterilized brown forest soil was added up to the liquid surface. Afterward, 0.1 ml of the above-mentioned J1 strain culture was added to each vial and each vial was completely sealed with a butyl rubber stopper and an aluminum seal. Shake culture was then carried out at 30° C. The decrease of TCE was determined at predetermined intervals analyzing the head space gas by gas chromatography.

Figure 7:
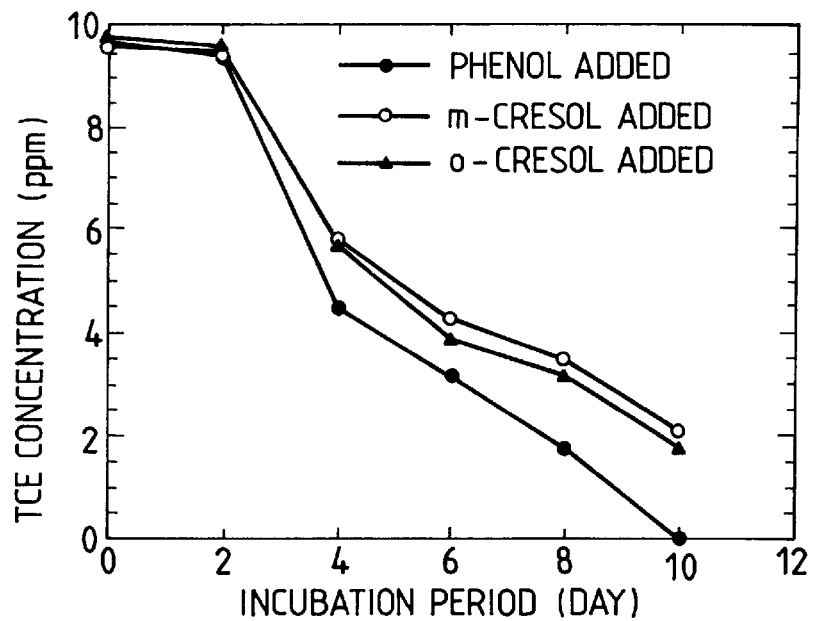
FIG. 7 is a graph showing the degradation of TCE in soil by strain J1 at 30° C.

The results are shown in FIG. 7.

When phenol was added as the inducer, TCE was finally degraded to the detection limit or below. Considering that the degradation occurred at the initial TCE concentration as high as about 10 ppm, the degradation activity of J1 strain is as good as that of the known TCE degrading bacteria.

EXAMPLE 7

Degradation of DCE in Soil by Strain J1

Figure 8:
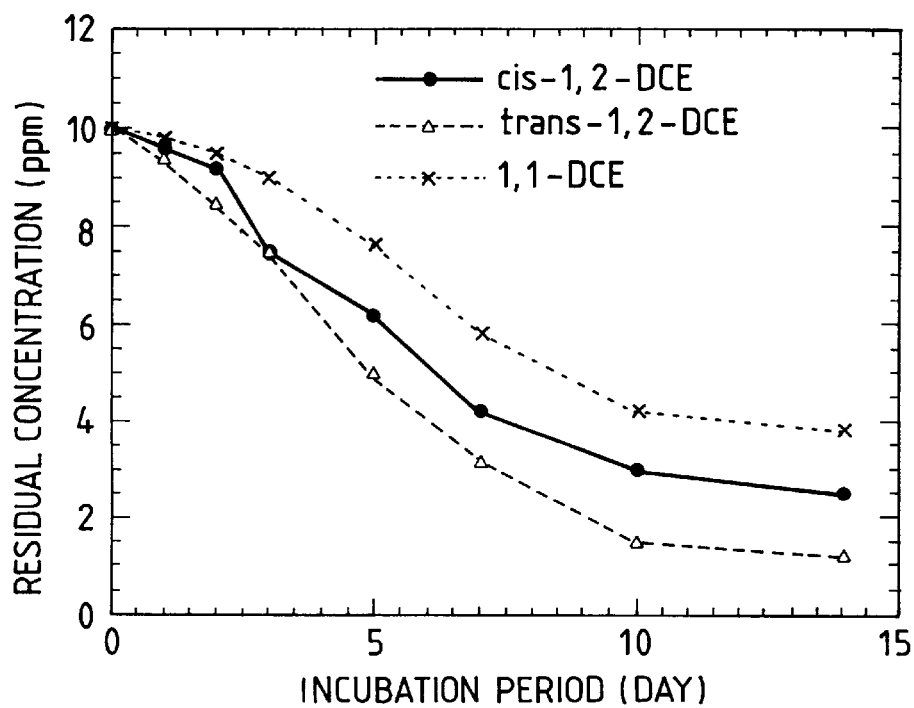
FIG. 8 is a graph showing the degradation of DCE in soil by strain J1 at 15° C.

The decrease of DCE was periodically measured in the same manner as in Example 4, except that the compound to be degraded was DCE (10 ppm). The result is shown in FIG. 8.

EXAMPLE 8

Degradation of TCE in Soil by Strain J1 (15° C.)

The same procedure as in Example 6 was carried out except that shake culture was carried out at 15° C. to evaluate the TCE degradation.

Figure 9:
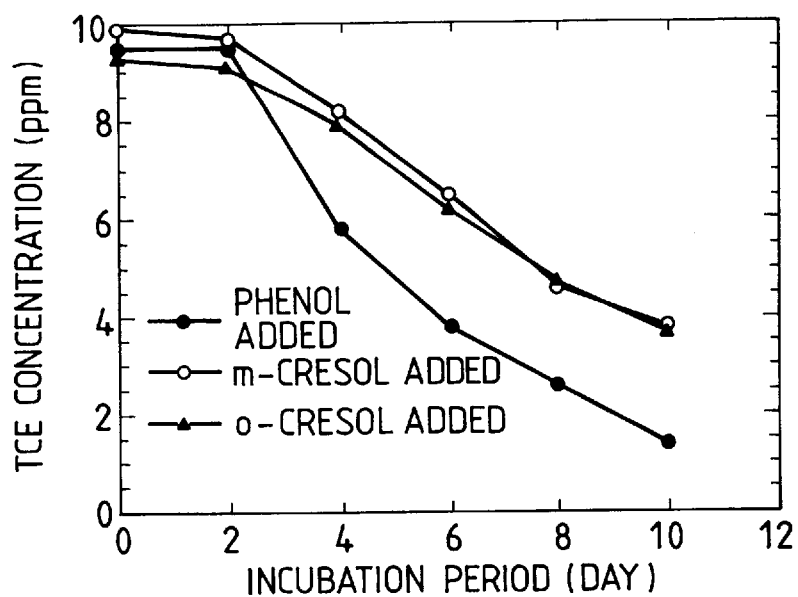
FIG. 9 is a graph showing the degradation of TCE in soil by strain J1 at 15° C.

The results are shown in FIG. 9.

As compared with incubation at 30° C., degradation was delayed by about 2 days, but even at a low temperature of 15° C., the TCE degradation activity was maintained within a practical level.

EXAMPLE 9

Purification of TCE-containing Gas Phase by Aerating Culture of Strain J1 (30° C.)

In a Sakaguchi flask, 50 ml of M9 medium was inoculated with a colony of J1 strain isolated on the M9 (0.2% sodium glutamate) agar medium, and shake culture was carried out at 30° C. for 24 hours.

Next, a vial containing 30 ml of M9 medium supplemented with 0.2% sodium glutamate and containing 100 ppm of phenol as an inducer was prepared and the vial was inoculated with 0.1 ml of the above-mentioned J1 culture.

A sample gas was prepared by passing air through a TCE-saturated solution, and the gas was introduced into the above medium at a flow rate of 60 ml/min for 30 minutes. The vial was then completely sealed with a butyl rubber stopper and an aluminum seal, and incubated with shaking at 30° C. The amount of TCE was determined at predetermined intervals by analyzing the head space gas by gas chromatography.

As a control, a vial not containing J1 cells was prepared, and the amount of TCE in the control was determined in the same manner. The residual ratio to the TCE amount of the control was calculated.

Figure 10:
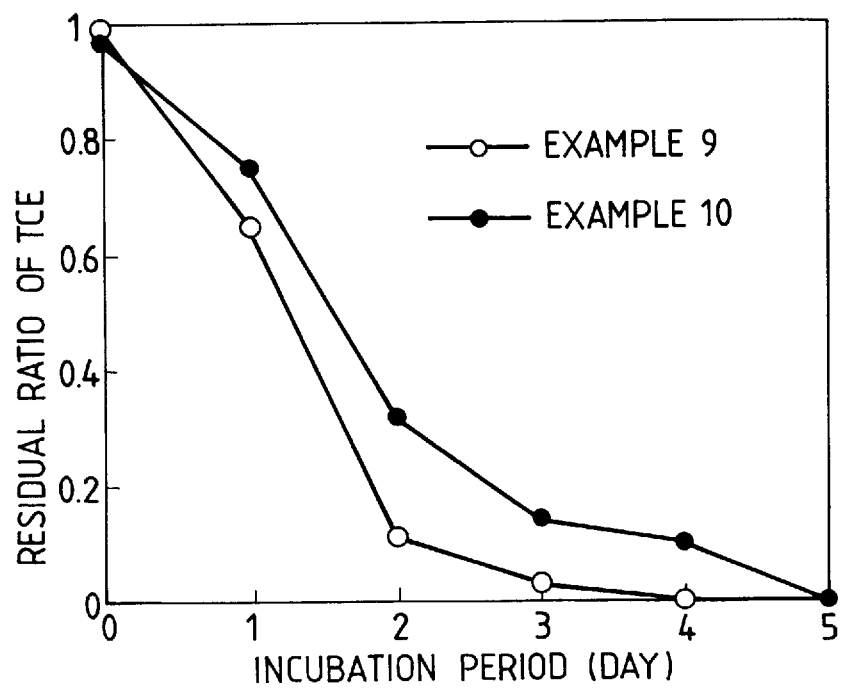
FIG. 10 is a graph showing the daily change of TCE residual ratio in Examples 9 and 10.

The results are shown in FIG. 10.

EXAMPLE 10

Purification of TCE-containing Gas Phase by Aerating Culture of Strain J1 (15° C.)

The same procedure as in Example 9 was carried out using the same culture, except that the temperature of incubation was 15° C. instead of 30° C. Similarly a control was prepared and tested at 15° C. The residual ratio to the TCE amount of the control was calculated.

The results are shown in FIG. 10.

EXAMPLE 11

Purification of DCE-containing Gas Phase by Aerating Culture of Strain J1

Figure 11:
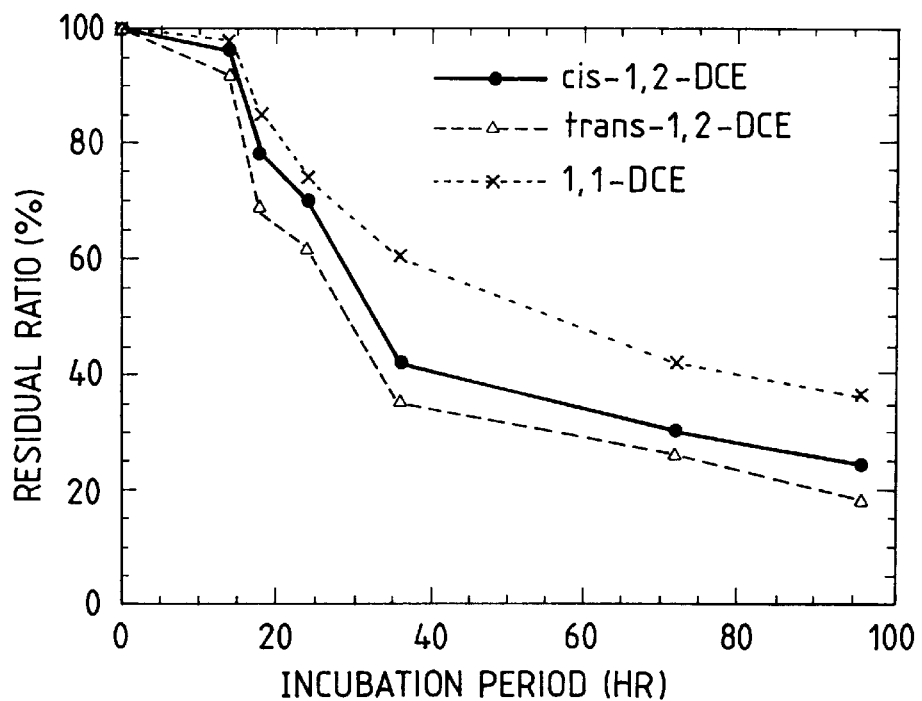
FIG. 11 is a graph showing the degradation of DCE in the gaseous phase by strain J1.

The decrease of dichloroethylene was measured periodically in the same manner as in Example 10, except that the compound to be degraded was cis-1,2-dichloroethylene (cis-1,2-DCE), trans-1,2-dichloroethylene (trans-1,2-DCE) or 1,1-dichloroethylene (1,1-DCE). The results are shown in FIG. 11.

EXAMPLE 12

Purification of TCE-containing Gas Phase by Aerating Soil Containing Strain J1 (30° C.)

The culture prepared in Example 9 was used and 0.1 ml of this culture was added to 30 ml of M9 medium (containing 0.2% sodium glutamate and 100 ppm of phenol as an inducer) in a vial, and a sterilized brown forest soil was added to the vial up to the liquid surface. Afterward, the vial was sealed with a butyl rubber stopper and then allowed to stand overnight at 30° C., and the excessive culture medium was removed by decantation. A TCE-containing gas was prepared by passing air through a TCE-saturated solution, and the gas was introduced into the vial at a flow rate of 60 ml/min for 30 minutes, and the vial was then completely sealed with the butyl rubber stopper and an aluminum seal, followed by incubation with shaking at 30° C. The amount of TCE was determined at predetermined intervals analyzing the head space gas by gas chromatography.

As a control, a similar experiment was carried out except that the system did not contain J1 cells. The amount of TCE in the control was determined in the same manner. The residual ratio of TCE to the control TCE amount was calculated.

Figure 12:
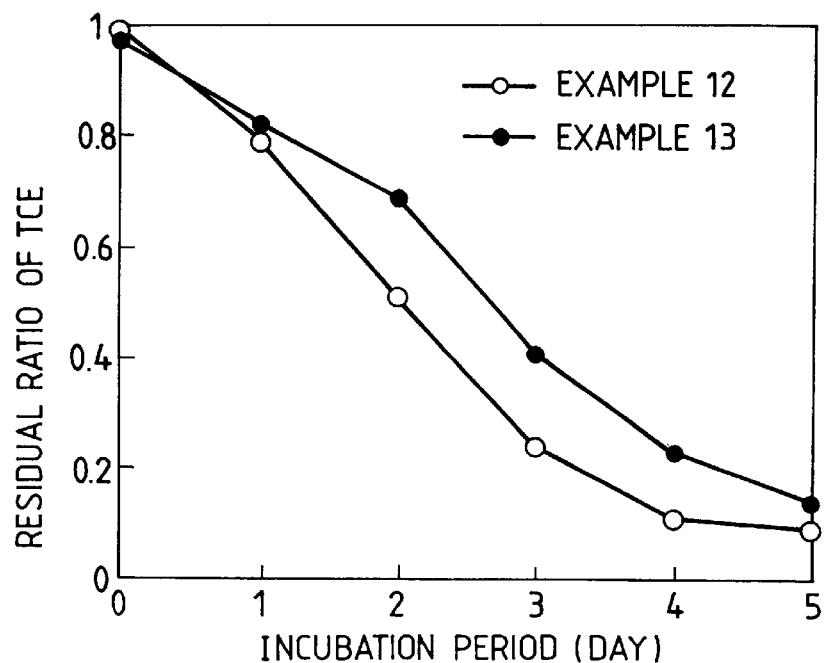
FIG. 12 is a graph showing the daily change of TCE residual ratio in Examples 12 and 13.

The results are shown in FIG. 12.

EXAMPLE 13

Purification of TCE-containing Gas Phase by Aerating Soil Containing Strain J1 (15° C.)

The same procedure as in Example 12 was carried out except that the temperature of incubation was 15° C. instead of 30° C. Similarly the residual ratio of TCE to the control TCE amount was calculated.

The results are shown in FIG. 12.

EXAMPLE 14

Purification of TCE-containing Gas Phase by Continuously Aerating Culture of Strain J1 (30° C.)

The culture prepared in Example 9 (0.1 ml) was added to 30 ml of M9 medium containing 0.2% sodium glutamate and 100 ppm of phenol as an inducer in a vial, and the vial was then completely sealed with a butyl rubber stopper and an aluminum seal. A sample gas was prepared by passing air through a TCE-saturated solution. The TCE-containing gas was continuously introduced into the medium in the standing vial at a flow rate of 0.5 ml/min at 30° C. The amount of TCE was measured at predetermined intervals by determining the amount of TCE in the exhausted air by gas chromatography.

As a control, a medium containing no J1 strain was used, and the amount of TCE of the control was determined in the same experimental system. The residual ratio to the control TCE amount was calculated.

Figure 13:
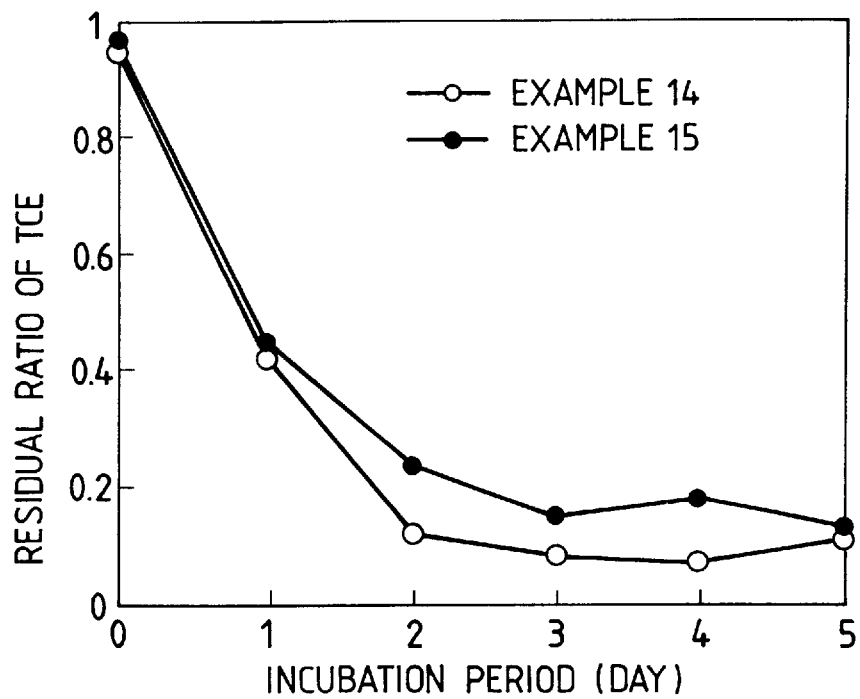
FIG. 13 is a graph showing the daily change of TCE residual ratio in Examples 14 and 15.

The results are shown in FIG. 13.

EXAMPLE 15

Purification of TCE-containing Gas Phase by Continuously Aerating Culture of Strain J1 (15° C.)

The same culture and the same procedure as in Example 14 were used except that the temperature of incubation was 15° C. instead of 30° C. to measure the amount of exhausted TCE at predetermined intervals. A control was tested in the same manner as in Example 14 except the incubation temperature. The residual ratio of TCE was calculated similarly.

The results are shown in FIG. 13.

EXAMPLE 16

Purification of TCE-containing Gas Phase by Continuously Aerating Soil Containing Culture of Strain J1 (30° C.)

The same culture in Example 9 (0.1 ml) was inoculated to 30 ml of M9 medium containing 0.2% sodium glutamate and 100 ppm of phenol as an inducer in a vial, and sterilized brown forest soil was then added thereto up to the liquid surface. Afterward, the vial was sealed with a butyl rubber stopper and allowed to stand overnight at 30° C. Then the excessive medium was removed by decantation. The vial was then completely sealed with the butyl rubber stopper and an aluminum seal and incubated at 30° C. A sample gas prepared by aerating air into a TCE-saturated solution was continuously introduced into the soil in the vial at a flow rate of 0.5 ml/min. The amount of TCE in the exhausted air was measured at predetermined intervals by gas chromatography.

The control vial did not contain J1 culture, and the amount of exhausted TCE from the control was determined in the same manner. The residual ratio of TCE to the control was calculated.

Figure 14:
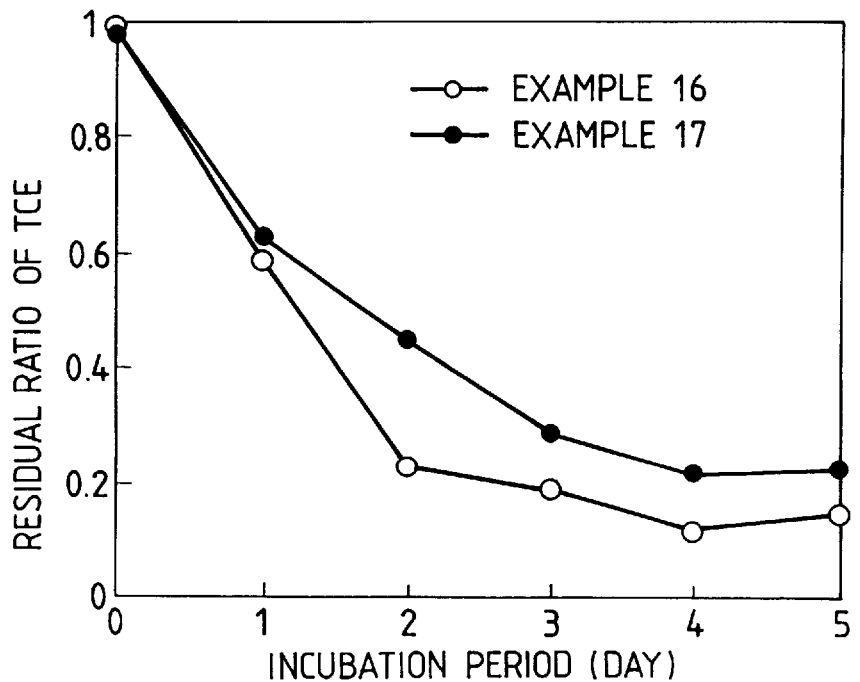
FIG. 14 is a graph showing the daily change of TCE residual ratio in Examples 16 and 17.

The results are shown in FIG. 14.

EXAMPLE 17

Purification of TCE-containing Gas Phase by Continuously Aerating Soil Containing Culture of Strain J1 (15° C.)

The same culture and the same procedure as in Example 16 were used except that the temperature of incubation was 15° C. instead of 30° C. to measure the amount of exhausted TCE at predetermined intervals. A control was tested in the same manner as in Example 16 except the incubation temperature.

The results are shown in FIG. 14.

As clearly shown in the above, novel bacterium of the present invention which can degrade aromatic compounds and/or chlorinated organic compounds enables the biological degradation of these compounds utilizing its growth characteristics different from those of conventional species, thus efficient biological treatment of waste water containing these compounds.

Furthermore, according to the present invention, there can be accomplished the remediation of soil polluted with aromatic compounds and/or chlorinated organic compounds, which has been difficult. Above all, the degradation activity of the bacterial strain at the actual soil temperature is hardly lowered in comparison with the degradation activity at the optimum temperature. Therefore, it is possible to provide an very practical method for remedying the polluted soil.

In addition, according to the present invention, the purification of a gas phase polluted with aromatic compounds and/or chlorinated organic compounds becomes possible, which has been heretofore practically impossible.

What is claimed is:

1. A method for biologically degrading at least one of aromatic compounds, dichloroethylene and trichloroethylene contained in a medium comprising the steps of:

inducing strain J1(FERM BP-5102) to have an enzymatic activity capable of degrading aromatic compounds, dichloroethylene and trichloroethylene by culturing strain J1 in the presence of an inducer, wherein said inducer is an aromatic compound capable of being degraded by said strain J1; and bringing the induced strain J1 (FERM BP-5102) into contact with the medium and decomposing at least one of the aromatic compounds, dichloroethylene and trichloroethylene contained in the medium.

2. The method according to claim 1, wherein the inducer is selected from the group consisting of phenol, o-cresol and m-cresol.

3. The method according to claim 1, wherein the medium is an aqueous medium.

4. The method according to claim 3, wherein the aqueous medium is brought into contact with the induced strain J1 which is immobilized on a carrier.

5. The method according to claim 4, wherein the induced strain J1 immobilized on the carrier is contained in a container having an inlet and an outlet, and the aqueous medium is introduced into the container from the inlet and removed from the container from the outlet.

6. The method according to any one of claims 3 to 5, wherein the aromatic compound is one or more compounds selected from the group consisting of phenol, o-cresol and m-cresol.

7. The method according to claim 1, wherein the medium is soil.

8. The method according to claim 7, wherein the degrading is carried out by introducing an aqueous medium containing the induced strain J1 into the soil and allowing proliferation of the induced strain J1, wherein said aqueous medium is supplemented with at least one of a nutrient and oxygen.

9. The method according to claim 8, wherein the introducing of the aqueous medium containing the induced strain J1 into the soil is carried out through a well made in the soil.

10. The method according to claim 7, wherein the contact is carried out by introducing the soil into an aqueous medium containing the induced strain J1.

11. The method according to claim 7, wherein the soil is brought into contact with the induced strain J1 immobilized on a carrier.

12. The method according to claim 1, wherein the medium is air.

13. The method according to claim 12, wherein the contact is carried out by introducing the air into an aqueous medium containing the induced strain J1.

14. The method according to claim 13, wherein the contact is carried out by bringing the air into contact with the induced strain J1 immobilized on a carrier.

15. The method according to claim 14, wherein the induced strain J1 is contained in a container having an inlet and an outlet, and the air is introduced into the container from the inlet and removed from the container from the outlet.

16. The method according to any one of claims 13 to 15, wherein at least one of trichloroethylene and dichloroethylene is degraded.

17. A method for biologically degrading at least one of aromatic compounds, dichloroethylene and trichlorethylene contained in a medium, comprising the steps of:

inducing strain J1 (FERM BP-5102) to have an enzymatic activity capable of degrading aromatic compounds, dichloroethylene and trichloroethylene by culturing strain J1 in the presence of an inducer, wherein said inducer is added to the medium; and bringing the induced strain J1 (FERM BP-5102) into contact with the medium and decomposing at least one of the aromatic compounds, dichloroethylene and trichloroethylene contained in the medium.

* * * * *